(12) United States Patent
Clopp et al.

(10) Patent No.: US 10,835,422 B2
(45) Date of Patent: Nov. 17, 2020

(54) TYMPANIC MEMBRANE PRESSURE EQUALIZATION TUBE

(71) Applicant: Tusker Medical, Inc., Menlo Park, CA (US)

(72) Inventors: Mathew D. Clopp, Santa Clara, CA (US); Scott J. Baron, Menlo Park, CA (US); Bernard H. Andreas, Los Altos, CA (US)

(73) Assignee: TUSKER MEDICAL, INC., Menlo Park, CA (US)

(*) Notice: Subject to any disclaimer, the term of this patent is extended or adjusted under 35 U.S.C. 154(b) by 420 days.

(21) Appl. No.: 15/892,855

(22) Filed: Feb. 9, 2018

(65) Prior Publication Data
US 2018/0161209 A1  Jun. 14, 2018

Related U.S. Application Data

(62) Division of application No. 14/668,071, filed on Mar. 25, 2015, now Pat. No. 9,907,700, which is a division
(Continued)

(51) Int. Cl.
*A61F 11/00* (2006.01)
*A61F 2/18* (2006.01)
*A61M 27/00* (2006.01)

(52) U.S. Cl.
CPC .............. *A61F 11/002* (2013.01); *A61F 2/18* (2013.01); *A61F 11/004* (2013.01); *A61M 27/002* (2013.01); *A61F 2002/183* (2013.01)

(58) Field of Classification Search
CPC ........ A61F 11/002; A61F 2/18; A61F 11/004; A61F 2002/183; A61F 2011/085;
(Continued)

(56) References Cited

U.S. PATENT DOCUMENTS 3,369,543 A * 2/1968 Ronco .................... B65D 47/42
                                                       604/2
3,530,860 A    9/1970 Majoros
(Continued)

FOREIGN PATENT DOCUMENTS

CN     101795646 A    8/2010
CN     102014795 A    4/2011
(Continued)

OTHER PUBLICATIONS

Office Action for Canadian Application No. 2,869,927, dated Oct. 15, 2019, 6 pages.
(Continued)

*Primary Examiner* — Adam Marcetich

(57) ABSTRACT

Systems, apparatus, and methods described herein relate to a tympanic membrane pressure equalization tube. The tympanic membrane pressure equalization tube can include a tubular body defining a lumen and having a proximal end and a distal end, where the tubular body is configured to be deployed in a tympanic membrane; and a fluid transport element disposed within the lumen and extending at least a length of the tubular body. The tubular body can be configured to transition from a first state in which the tubular body can be disposed within an introducer and a second state in which the tubular body can be retained in an incision formed the tympanic membrane after deployment, and the fluid transport element can enable transport of a fluid across the tympanic membrane.

19 Claims, 8 Drawing Sheets

Related U.S. Application Data of application No. 13/800,113, filed on Mar. 13, 2013, now Pat. No. 9,011,363.

(60) Provisional application No. 61/622,274, filed on Apr. 10, 2012.

(58) Field of Classification Search
CPC .... A61M 27/002; A61J 1/2068; A61J 1/2072; A61J 1/2075; B43K 8/02; B43K 8/04; B43K 8/022; B43K 8/024; B43K 8/026; B43K 1/003; B43K 1/006; B43K 8/06; B43K 8/08

See application file for complete search history.

(56) References Cited

U.S. PATENT DOCUMENTS

| | | | |
|---|---|---|---|
| 3,807,409 A | 4/1974 | Paparella et al. | |
| 3,871,380 A | 3/1975 | Heros | |
| 3,948,271 A | 4/1976 | Akiyama | |
| 4,094,303 A * | 6/1978 | Johnston | A61F 11/002 |
| | | | 128/867 |
| 4,159,719 A * | 7/1979 | Haerr | A61M 31/00 |
| | | | 128/865 |
| 4,168,697 A | 9/1979 | Cantekin | |
| D274,753 S | 7/1984 | Armstrong | |
| 4,509,876 A * | 4/1985 | Hori | B43K 5/18 |
| | | | 401/151 |
| 4,568,337 A | 2/1986 | Treharne et al. | |
| 4,695,275 A | 9/1987 | Bruce et al. | |
| 4,764,168 A | 8/1988 | Suh | |
| 4,775,370 A | 10/1988 | Berry | |
| 5,092,837 A | 3/1992 | Ritch et al. | |
| 5,139,502 A | 8/1992 | Berg et al. | |
| 5,163,925 A * | 11/1992 | Mukai | A61F 11/002 |
| | | | 128/864 |
| 5,207,685 A | 5/1993 | Cinberg et al. | |
| 5,246,455 A | 9/1993 | Shikani | |
| 5,334,179 A * | 8/1994 | Poli | A61J 1/2089 |
| | | | 604/403 |
| 5,489,286 A | 2/1996 | Cinberg et al. | |
| D371,606 S | 7/1996 | Doyle | |
| D379,505 S | 5/1997 | Doyle | |
| 5,645,584 A | 7/1997 | Suyama | |
| 5,649,932 A | 7/1997 | Fouin et al. | |
| 5,775,336 A | 7/1998 | Morris | |
| 5,851,199 A | 12/1998 | Peerless et al. | |
| D405,173 S | 2/1999 | Falco | |
| 5,976,151 A * | 11/1999 | Siegbahn | A61F 2/203 |
| | | | 606/108 |
| 6,027,532 A * | 2/2000 | Hobeika | A61F 11/002 |
| | | | 606/109 |
| 6,042,574 A | 3/2000 | O'Halloran | |
| 6,045,528 A * | 4/2000 | Arenberg | A61F 11/002 |
| | | | 604/28 |
| 6,120,484 A * | 9/2000 | Silverstein | A61F 11/00 |
| | | | 424/427 |
| D440,314 S | 4/2001 | Barnard | |
| 6,939,494 B2 | 9/2005 | Goode et al. | |
| 7,097,661 B2 | 8/2006 | Perry | |
| 7,850,455 B2 | 12/2010 | Cottler et al. | |
| 8,052,693 B2 | 11/2011 | Shahoian | |
| 8,197,433 B2 | 6/2012 | Cohen | |
| 8,425,488 B2 | 4/2013 | Clifford et al. | |
| 8,480,610 B1 | 7/2013 | Hill | |
| D707,822 S | 6/2014 | Clopp et al. | |
| 9,011,363 B2 | 4/2015 | Clopp et al. | |
| 9,326,943 B1 | 5/2016 | Skovlund | |
| 9,907,700 B2 | 3/2018 | Clopp et al. | |
| 2002/0058898 A1 | 5/2002 | Goode et al. | |
| 2002/0082627 A1 | 6/2002 | Berg et al. | |
| 2003/0018291 A1 | 1/2003 | Hill et al. | |
| 2003/0187456 A1 | 10/2003 | Perry | |
| 2004/0204759 A1 | 10/2004 | Blom et al. | |
| 2005/0075733 A1 | 4/2005 | D'Eredita | |
| 2008/0003205 A1 | 1/2008 | Bonassar et al. | |
| 2008/0058832 A1 | 3/2008 | Fujiwara | |
| 2008/0262505 A1 | 10/2008 | Shahoian | |
| 2008/0294255 A1 | 11/2008 | Gonzales | |
| 2009/0088677 A1 | 4/2009 | Cohen | |
| 2009/0209972 A1 | 8/2009 | Loushin et al. | |
| 2009/0226240 A1 * | 9/2009 | Rolion | B43K 1/003 |
| | | | 401/198 |
| 2010/0030131 A1 * | 2/2010 | Morriss | A61M 1/0088 |
| | | | 604/21 |
| 2010/0230447 A1 * | 9/2010 | Eriksen | B65D 47/40 |
| | | | 222/481.5 |
| 2011/0015612 A1 | 1/2011 | Arcand et al. | |
| 2011/0015645 A1 | 1/2011 | Liu et al. | |
| 2011/0208161 A1 * | 8/2011 | Ivri | A61K 9/0009 |
| | | | 604/514 |
| 2011/0288559 A1 | 11/2011 | Shahoian | |
| 2012/0136294 A1 | 5/2012 | Gonzales | |
| 2014/0252662 A1 * | 9/2014 | Graham | B01F 3/04794 |
| | | | 261/76 |
| 2015/0196430 A1 | 7/2015 | Clopp et al. | |
| 2019/0321610 A1 | 10/2019 | Goldfarb et al. | |

FOREIGN PATENT DOCUMENTS

| | | |
|---|---|---|
| CN | 102510746 A | 6/2012 |
| DE | 102010028705 | 11/2011 |
| EP | 1415671 A1 | 5/2004 |
| WO | WO 97/17918 | 5/1997 |
| WO | WO 2003/013361 | 2/2003 |
| WO | WO 2011/008948 | 1/2011 |
| WO | WO 2011/019954 | 2/2011 |
| WO | WO 2013/155169 | 10/2013 |
| WO | WO 2014/160398 | 10/2014 |
| WO | WO 2015/168642 | 11/2015 |

OTHER PUBLICATIONS

Notice of Final Rejection for Korean Application No. 10-2014-7031224, dated Nov. 27, 2019, 6 pages.
Office Action for Canadian Application No. 2,869,927, dated Feb. 27, 2019, 4 pages.
Notice of Preliminary Rejection for Korean Application No. 10-2014-7031224, dated May 27, 2019, 11 pages.
First Office Action and Search Report for Chinese Application No. 201380019310.1, dated Nov. 23, 2015, 7 pages.
Office Action for European Application No. 13718264.8, dated Feb. 23, 2018, 5 pages.
Office Action for Mexican Application No. MX/a/2014/012237, dated Sep. 27, 2016, 3 pages.
Office Action for U.S. Appl. No. 13/800,113, dated Aug. 19, 2014, 13 pages.
International Search Report and Written Opinion for International Application No. PCT/US2013/035953, dated Sep. 23, 2013.
Office Action for U.S. Appl. No. 14/668,071, dated Feb. 9, 2017, 10 pages.
Office Action for U.S. Appl. No. 14/668,071, dated Jul. 24, 2017, 18 pages.
JEDMED, Brochure, Jan. 2011, 2 pages, St. Louis, Missouri, USA, www.jedmed.com.
Grace Medical, Brochure, 2007, 2 pages, Memphis, Tennessee, USA, www.gracemedical.com.

* cited by examiner

TYMPANIC MEMBRANE PRESSURE EQUALIZATION TUBE

This application is a divisional of U.S. patent application Ser. No. 14/668,071, entitled "Tympanic Membrane Pressure Equalization Tube," filed Mar. 25, 2015, which is a divisional of U.S. patent application Ser. No. 13/800,113, entitled "Tympanic Membrane Pressure Equalization Tube," filed Mar. 3, 2013 (now U.S. Pat. No. 9,011,363), which claims priority to U.S. Pat. App. No. 61/622,274, entitled "Tympanic Membrane Pressure Equalization Tube," filed Apr. 10, 2012, the disclosures of each are incorporated by reference herein.

FIELD OF THE INVENTION

The present invention is generally related to medical devices and apparatus. In particular, the invention provides systems and methods for delivering a pressure equalization tube to a tympanic membrane of an ear.

BACKGROUND OF THE INVENTION

Otitis media is among the most common diagnoses made by pediatricians. A majority of children may have at least one episode of otitis media ("earache") prior to their third birthday. Otitis media is often caused by an inability of the eustachian tube to drain fluid from the middle ear. Otitis media is often treated with antibiotics.

A significant number of children exhibit recurrent episodes of otitis media and/or otitis media with effusion. Treatment of these more severe cases often involves the placement of a tympanostomy tube through the tympanic membrane to provide adequate drainage of the middle ear and reduce the likelihood of future infections. Tympanostomy tubes provide fluid communication between the middle and outer ear (e.g., pressure equalization) and typically fall out spontaneously within about a year of placement. Tympanostomy tube placement is among the most frequent surgical procedures performed in the pediatric population. It has been estimated that more than a million tympanostomy tubes may be placed each year, with typical patients being between about 18 months and 7 years of age at the time of the procedure.

Tympanostomy tube placement is typically performed in an out-patient surgery setting under general anesthesia. The physician typically first examines the external auditory canal and tympanic membrane under microscopic visualization through a hand-held conical shaped speculum. The physician then makes an incision in the tympanic membrane (a "myringotomy"), typically using a standard, small profile scalpel which the physician advances through the conical speculum. In many cases, the physician will then place the tympanostomy tube through the tympanic membrane, typically using a basic tool for holding and advancing the tube into the myringotomy. The physician may then pass a suction device through the tube, into the middle ear, to aspirate fluid/effusion from the middle ear.

A wide variety of tympanostomy tubes is commercially available, and a still wider variety of other tubes has been proposed. Systems have also been proposed to both perform the myringotomy and deploy the tympanostomy tube with a single treatment assembly. In recent years, more complex and expensive systems have been proposed for diagnosis or treatment of the tissues of the ear, including systems using laser energy for forming a myringotomy, video systems for imaging of the ear canal, and the like. These various proposed alternatives for tympanostomy tubes and tube placement systems have met with varying degrees of acceptance. Some proposed alternatives have been overly complex, overly expensive and/or ineffective. Thus, to date, standard tubes and tube placement procedures and devices have primarily used.

Improved devices, systems, and methods for delivering pressure equalization tubes to a tympanic membrane without requiring multiple devices and operator-performed steps can be found in US Patent Publication No. 2011/0015645 which is incorporated by reference herein in its entirety. A system for automatically puncturing and delivering a tympanic membrane equalization tube (i.e., tympanostomy tube) is described. The system can be used to deliver a wide variety of pressure equalization tubes to the tympanic membrane. The current invention is directed to one such tube, which has been specifically designed to remain in the tympanic membrane for a prolonged period of time.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements.

BRIEF SUMMARY OF THE INVENTION

The present invention provides a specifically designed pressure equalization tube that can be delivered to the tympanic membrane.

In one embodiment, a tympanic membrane pressure equalization tube comprises a tubular body with a distal end and a proximal end and a lumen therebetween, a medial flange located at the distal end of the tube, where the medial flange comprises 3 retention elements and a space between each wing, and a lateral flange that is located at the proximal end of the tube. The outside diameter of the medial flange is greater than the outside diameter of the lateral flange and the diameter of the medial flange is between about 2.0 mm and about 5.0 mm and the diameter of the lateral flange is between about 1.75 mm and about 4.0 mm.

In another embodiment, the outside diameter of the medial flange is between about 3.0 mm and about 4.0 mm and the outside diameter of the lateral flange is between about 2.0 mm and about 3.0 mm.

In another embodiment, the medial flange retention elements are of equal size and shape.

In still another embodiment the medial flange retention elements have a width of between about 0.6 mm and 1.0 mm or of about 0.8 mm.

In a further embodiment, the medial flange retention elements have a length of between about 1.0 mm and 3.0 mm or of between about 1.8 mm and 1.9 mm.

In another embodiment, the lateral flange comprises two retention elements.

In another aspect, the invention is a method for placing a pressure equalization tube within the tympanic membrane of a patient. The method comprises providing a pressure equalization tube in an uncompressed state, the pressure equalization tube having a tubular body with a distal end and a proximal end and a lumen therebetween and that has a compressed state and an uncompressed state. The pressure equalization tube further comprises a medial flange located at the distal end of the tubular body, the medial flange comprising 3 retention elements and a space between each retention element, and a lateral flange located at the proximal end of the tubular body. The outside diameter of the medial flange is greater than the outside diameter of the lateral flange and the diameter of the medial flange is between about 2.0 and 5.0 mm and the diameter of the lateral flange is between about 1.75 mm and 4.0 mm. When the tube is in the uncompressed state, the medial flange retention members are aligned perpendicularly to the tube lumen and in the compressed state the medial flange retention members are aligned longitudinally to the tube lumen. The method further comprises compressing the pressure equalization tube into a compressed form wherein the medial flange retention members are longitudinally aligned with the pressure equalization tube lumen into a pressure equalization tube delivery device and do not overlap one with the other, advancing the pressure equalization tube into the tympanic membrane such that the medial flange is located medially of the tympanic membrane and the lateral flange is located laterally of the tympanic membrane and the pressure equalization tube is returned to its uncompressed form.

In one embodiment of the method, the outside diameter of the medial flange is between about 3.0 and about 4.0 mm and the outside diameter of the lateral flange is between about 2.0 mm and about 3.0 mm.

In another embodiment of the method, the medial flange retention elements are of equal size and shape.

In a further embodiment of the method, the medial flange retention elements have a width of between about 0.6 mm and 1.0 mm.

In still another embodiment of the method, the medial flange retention elements have a width of about 0.8 mm.

In yet another embodiment of the method, the medial flange retention elements have a length of between about 1.0 mm and 3.0 mm.

In another embodiment of the method, the medial flange retention elements have a length of between about 1.8 mm and 1.9 mm.

In a further embodiment of the method, the lateral flange comprises two retention elements.

In another embodiment of the method, the lateral flange retention elements are of equal size and shape.

In another aspect, the invention is directed to a tympanic membrane pressure equalization tube system comprising a tympanic membrane pressure equalization tube and an introducer. The tympanic membrane pressure equalization tube comprises a tubular body with a distal end and a proximal end and a lumen therebetween, a medial flange located at the distal end of the tubular body, said medial flange comprising two or more retention elements and a space between each retention element. The introducer comprises a cylindrical member with an inner surface. The inner surface has an inner surface circumference. The retention elements are of equal size and shape and the maximum length of each retention element is equal to the inner surface circumference of the introducer divided by the number of retention elements.

In another embodiment the system comprises three retention elements and in another embodiment, the system comprises a lateral flange located at the proximal end of the tubular body.

In still another aspect, the invention is directed to a tympanic membrane pressure equalization tube comprising a tubular body with a distal end and a proximal end and a lumen therebetween, and a helical coil surrounding the tubular body. The helical coil comprises multiple raised ribs for retention of the pressure equalization tube in the tympanic membrane.

In a further aspect, the invention is directed to a tympanic membrane pressure equalization tube comprising a tubular body with a distal end and a proximal end and a lumen therebetween. The lumen of the tubular body is lined with artificial cilia to aid the transport and expulsion of effusion from the middle ear.

In another aspect, the invention is directed to a tympanic membrane pressure equalization tube comprising a tubular body with a distal end and a proximal end and a lumen therebetween and a structure selected from the group consisting of a vent lumen and a wick that would aid in effusion removal during deployment of the pressure equalization tube.

In yet another aspect, the invention is directed to a tympanic membrane pressure equalization tube comprising a tubular body with a distal end and a proximal end and a lumen therebetween, a medial flange located at the distal end of the tubular body, the medial flange comprising a cutting edge; and a lateral flange located at the proximal end of the tubular body. The tympanic membrane pressure equalization tube is made from a shape memory material that is pre-shaped with the cutting edge closed and centered on the medial flange and will self-dilate following deployment.

For a further understanding of the nature and advantages of the invention, reference should be made to the following description taken in conjunction with the accompanying figures. However, each of the figures is provided for the purpose of illustration and description only and is not intended to limit the scope of the embodiments of the present invention.

DETAILED DESCRIPTION OF THE INVENTION

Figure 1:
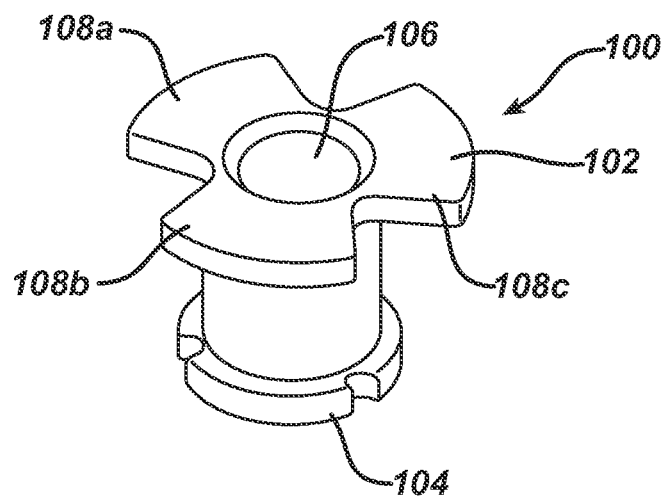
FIG. 1 is a perspective view of a pressure equalization tube according to one embodiment of the invention.
Figure 2:
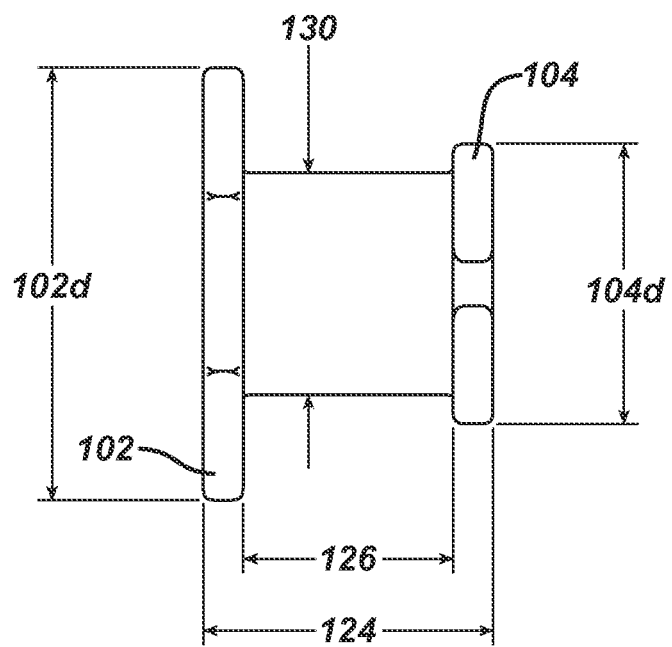
FIG. 2 is a side view of the pressure equalization tube of FIG. 1.

The following detailed description should be read with reference to the drawing, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to made and use the invention, and describes several embodiments, adaptations, variations, alternatives and uses of the invention, including what is presently believed to be the best mode of carrying out the invention.

As used herein, the terms "about" and "approximately" for any numerical values or ranges indicate a suitable dimensional tolerance that allows the part of collection of components for function for its intended purpose as described herein.

The tympanic membrane pressure equalization tube according to the invention is a grommet like device which is folded and/or compressed within the tube, and recovers its shape when delivered into the tympanic membrane.

Embodiments of the invention are compatible for use with a suite of medical devices for visualizing the tympanic membrane, puncturing the tympanic membrane, and anesthetizing the tympanic membrane. Examples of such medical devices are shown in co-assigned U.S. patent application Ser. No. 11/749,733, the entirety of which is incorporated by reference. Accordingly, aspects of U.S. patent application Ser. No. 11/749,733 may be integrated, combined, and used in conjunction with the embodiments disclosed herein.

Figure 3:
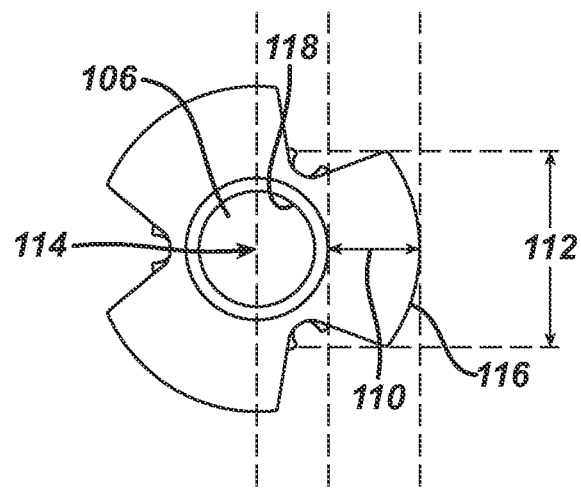
FIG. 3 is a top view of the pressure equalization tube of FIG. 1.

FIGS. 1 through 4 show a tympanic membrane pressure equalization tube 100, also referred to herein as a pressure equalization tube, a PE tube or a tympanostomy tube, according to one embodiment of the invention. In this embodiment, referring to FIG. 1, the tube 100 is configured as a tubular body with asymmetric flanges, a medial flange 102 a lateral flange 104 and a tube lumen 106. The medial flange 102 has a larger diameter 102d than the lateral flange 104 diameter 104d (see FIG. 2). The medial flange 102 has three retention elements of equal size and shape, retention elements 108a, 108b and 108c. As shown in FIG. 3, these retention elements have a width 110 of between about 0.6 mm and 1.0 mm, or about 0.80 mm, a length 112 of between about 1.0 mm and 3.0 mm, or of between about 1.8 mm and 1.9 mm, or about 1.87 mm and are spaced evenly around the circumference of the tubular body lumen 106, that is, the retention elements are spaced 120° apart. The medial flange outside diameter 102d is between about 2.0 mm and about 5.0 mm or between about 3.0 mm and 4.0 mm or about 2.11 mm. The distance from the center 114 of the tube lumen 106 to the outer edge 116 of the medial flange 102 is 3.25 mm and from the center 114 of the tube lumen 106 to the inside edge 118 of the medial flange 102 is 1.65 mm.

Figure 4:
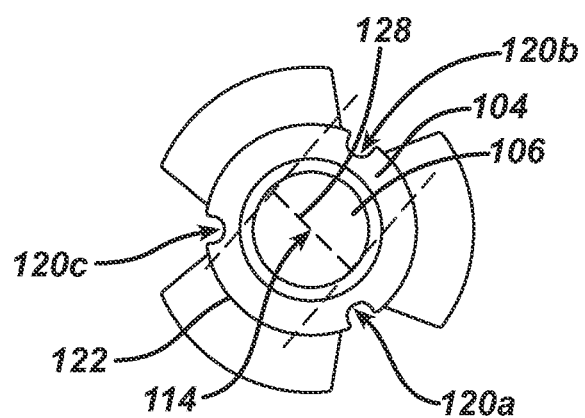
FIG. 4 is a bottom view of the pressure equalization tube of FIG. 1.
Figure 5:
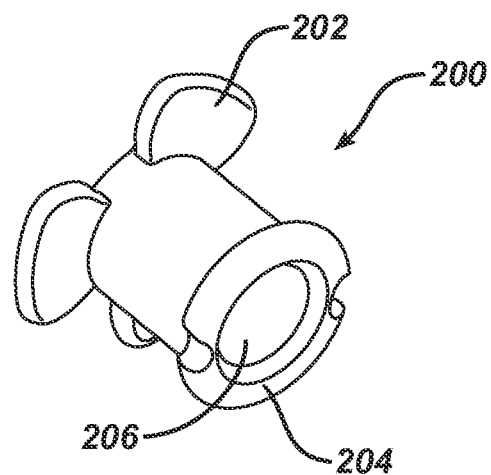
FIG. 5 is a perspective view of a pressure equalization tube according to a second embodiment of the invention.
Figure 6:
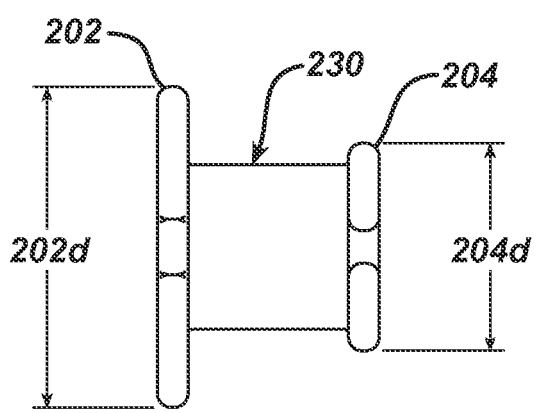
FIG. 6 is a side view of the pressure equalization tube of FIG. 5.
Figure 7:
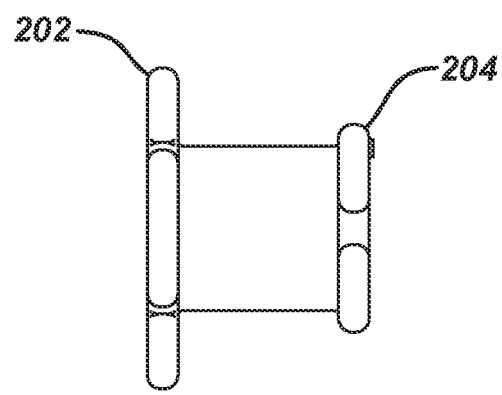
FIG. 7 is a side view of the pressure equalization tube of FIG. 5, from the opposite side shown in FIG. 6.

Referring now to FIG. 4, a second, lateral flange 104 is smaller than the medial flange 102 and is uniform in width with three retention elements and three notches 120a, 120b and 120c that are spaced 120° apart, with each notch 120a, 120b, and 120c at the same location as, or circumferentially aligned with the spaces between the medial flange retention elements 108a, 108b and 108c. The distance from the center 114 of the tube lumen 106 to the outside edge 122 of the lateral flange 104, the outer diameter of the lateral flange is between about 1.75 mm and about 4.0 mm or between about 2.0 mm and 3.0 mm or about 2.11 mm.

Figure 8:
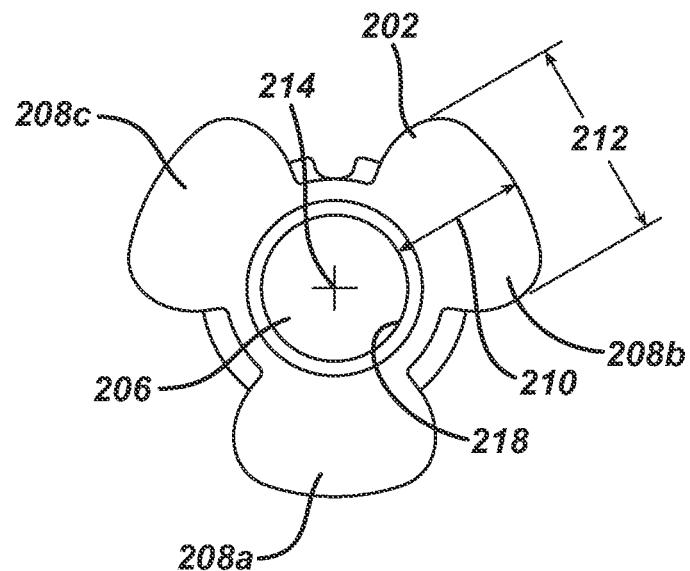
FIG. 8 is a top view of the pressure equalization tube of FIG. 5.

FIGS. 5 through 9 show a tympanic membrane pressure equalization tube 200 according to a second embodiment of the invention. In this embodiment, referring to FIG. 5, the pressure equalization tube 200 is configured as a tubular body 230 with asymmetric flanges, medial flange 202 a lateral flange 204 and a lumen 206. The medial flange 202 has a larger outer diameter 202d than the lateral flange 204 outer diameter 204d (see FIGS. 6 and 7). The medial flange 202 has three equal retention elements 208a, 208b and 208c. As shown in FIG. 8, these retention elements have a width 210 of between about 0.6 mm and 1.0 mm, or about 0.80 mm, a length 212 of between about 1.0 mm and 3.0 mm, or of between about 1.8 mm and 1.9 mm, or about 1.87 mm and are spaced evenly around the circumference of the tube lumen 206, that is, the wings are spaced 120° apart. The medial flange outside diameter 202d is between about 2.0 mm and about 5.0 mm or between about 3.0 mm and 4.0 mm or about 2.11 mm. The distance from the center 214 of the tube lumen 206 to the outer edge 216 of the medial flange 202 is 3.25 mm and from the center 214 of the tube lumen 206 to the inside edge 218 of the medial flange 202 is 1.65 mm.

Figure 9:
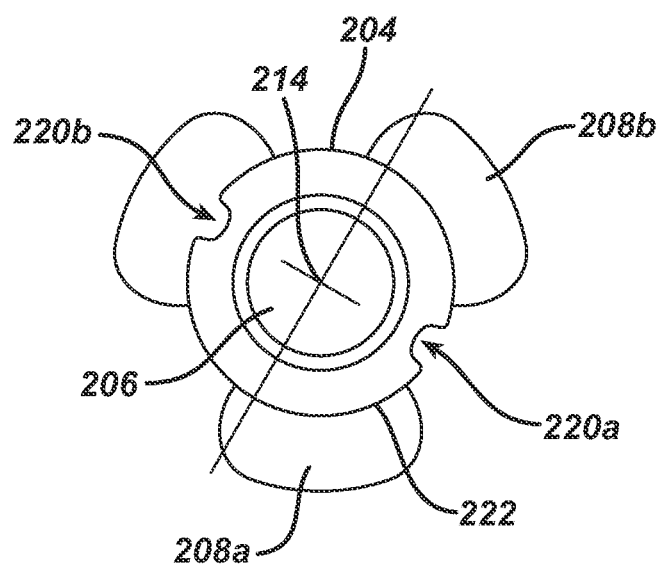
FIG. 9 is a bottom view of the pressure equalization tube of FIG. 5.

Referring now to FIG. 9, a second, lateral flange 204 is smaller than the medial flange 202 and is uniform in width with two notches 220a and 220b and spaced 180° apart, with notch 220a be at the same location as the spaces between the medial flange wings 208a and 208b. The distance from the center 214 of the tube lumen 206 to the outside edge 222 of the lateral flange 204, the outer diameter of the lateral flange is between about 1.75 mm and about 4.0 mm or between about 2.0 mm and 3.0 mm or about 2.11 mm.

The tympanic membrane pressure equalization tube according to the invention may comprise a shape memory material that can be mechanically compressed but can substantially return to an uncompressed state. Examples of materials that can be mechanically deformed but can return to an uncompressed state when not mechanically stressed include a number of biocompatible metals such as titanium, silver, tantalum, alloys of stainless steel, cobalt, chromium, and alumina and polymers or other pliable elastomeric materials such as polyolefins, polyurethanes, silicone rubber, PEEK, PMMA, and fluoropolymers. The tube 100 is often made of silicone rubber and may have an axial length of between about 2.0 mm and about 2.5 mm and in the embodiment shown in FIG. 2 the axial length is about 2.2 mm. The thickness of each of the lateral 104 flange and the medial flange 102 is between about 0.25 mm and 0.35 mm or is approximately 0.30 mm and the flange to flange length 126 of the tube 100 is between about 1.0 mm and 2.0 mm or is about 1.6 mm. The tube 100 may have an inner diameter of between about 1.0 mm and about 1.5 mm, and in the embodiment shown in FIG. 2, the inner diameter is about 1.1 mm and the outer diameter may be between about 1.5 mm and 2.0 mm and is about 1.7 mm.

In order to deliver a tympanic membrane equalization tube to the tympanic membrane, the tube may be folded down and compressed into an introducer for storage until deployment into a patient's tympanic membrane. For certain tubes, particularly those made of silicone rubber, two-undesirable effects may occur when the tube is highly compressed and forced to contact itself. The first is that blocking may occur, that is the tacky surfaces of the tube may cause the tubes to temporarily self adhere one to the other. Blocking can deform the shape of a silicone object by having its surfaces contact one another, holding the object in something other than its natural free state. Blocking typically does not permanently change the shape of the object and the natural stresses in the object will have a tendency to overcome the blocking surface tension to restore the object to its original shape. The release may take a relatively long period of time (i.e. greater than 1 second). Further, the tube may become compression set, that is, the natural shape of the tube may be permanently deformed due to stress relief of the material. The stress relief can happen due to high stresses being applied for long periods of time, changing the natural unstressed shape.

In order to overcome the blocking and compression effects, in one embodiment of the invention, the retention elements (i.e. 308a, 308b and 308c shown in FIG. 10) of the tympanic membrane equalization tubes 300 are designed to prevent touching of the edges when it they are folded down and compressed into the introducer for storage and therefore to mitigate areas of adhesion that may cause blocking. The relationship of the retention elements to the introducer 320 is described below.

Figure 10:
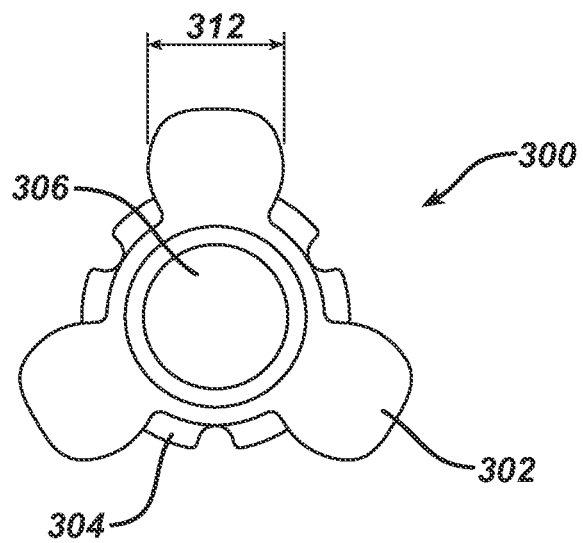
FIG. 10 is a top view of a pressure equalization tube according to further embodiment of the invention.
Figure 11:
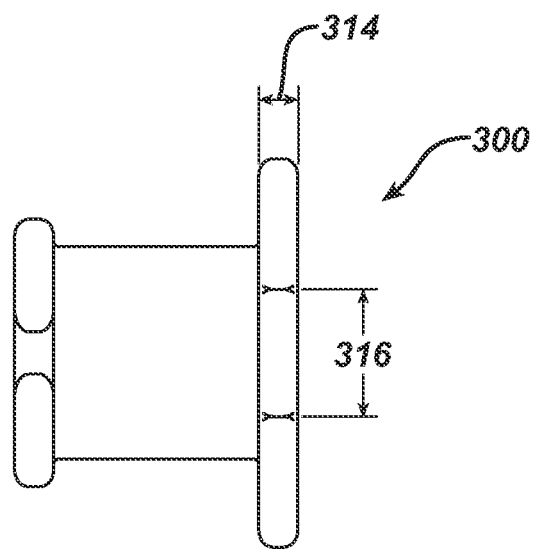
FIG. 11 is a side view of the pressure equalization tube of FIG. 10.
Figure 12:
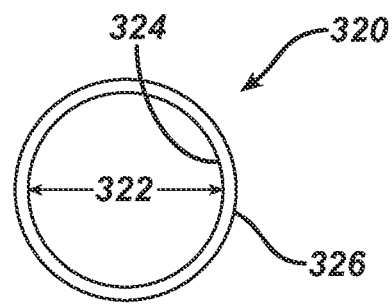
FIG. 12 is a cross-section view of an introducer useful for introducing a pressure equalization tube according to the invention.

FIGS. 10 and 11 show a tympanic membrane pressure equalization tube 300 according to a further embodiment of the invention, and FIG. 12 shows cross-sectional view of an introducer 320 for the tympanic membrane pressure equalization tube 300. The introducer has an inside surface 324, and outside surface 326 and an inner diameter 322. In this embodiment, referring to FIG. 10, the tube 300 is configured as a tubular body with asymmetric flanges, a medial flange 302 a lateral flange 304 and a tube lumen 306, although tubes without a lateral flange are also contemplated according to the invention. The medial flange 302 has a larger diameter than the lateral flange 304. The medial flange 302 has three retention elements of equal size and shape, retention elements 308a, 308b and 308c, although according to the invention, the tube may include two, three, four or more retention elements. As shown in FIG. 10, these retention elements have a length 312 of between about 0.6 mm and 1 mm, or about 1 mm such that when the three elements are collapsed they are smaller than the circumference of the inside surface 324 of the introducer 320 (see FIG. 12). In the particular embodiment shown in FIGS. 10 and 11, the thickness 314 of the medial flange 302 is 0.305 mm. Accordingly, the length 312 of the retention elements can be calculated as follows (L):

Compressed collapsed inner diameter of tube 300=A
Thickness of Retention Element=B
Inner diameter 322 of introducer 320=C
Collapsed circumference of tube 300=D $$A=C-2B$$

$$D=A*\pi$$

$$L=D/3$$

For the embodiment shown in FIGS. 10 and 11, C=1.55 mm, B=0.305 mm, A=0.94 mm, D=2.95 mm and L=0.98 mm. The maximum length 312 of the retention elements in this instance is 0.98 mm, and the length may be between about 0.6 and 1 mm. In this embodiment, the retention elements are of equal size and shape and the maximum length of each retention element is equal to the circumference of the inside surface 324 of the introducer 320 divided by the number of retention elements.

Another method to reduce retention element adhesion according to the invention is to add a coating to the tube. A thin coating (0.25 μm) of parylene or other similar biocompatible coating can be applied to reduce retention element adhesion and ensure near instantaneous opening and rapid tube deployment (i.e. within 1 second).

Figure 13:
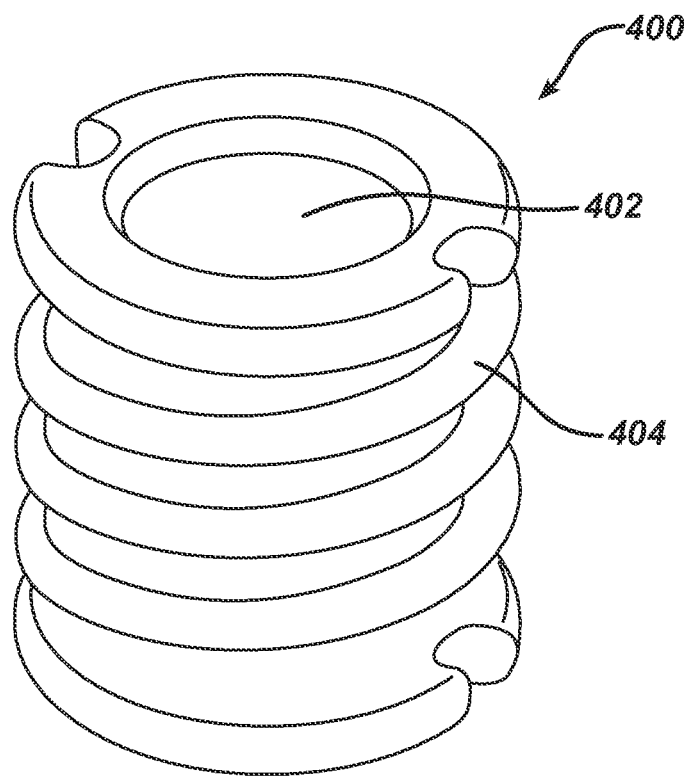
FIG. 13 is a perspective view of a pressure equalization tube according to another embodiment of the invention.

Another embodiment of a pressure equalization tube according to the invention is shown in FIG. 13. Rather than flanges at each end of the tube, the pressure equalization tube 400 comprises a helical tube. Surrounding the tubular body lumen 402, on the surface of the pressure equalization tube 400 is a helical coil 404 that is a raised rib wrapped in a helical spiral. The tube 400 is retained in the patient's tympanic membrane by means of the multiple raised ribs that surround the tube 400. In this particular embodiment, the inner diameter of the pressure equalization tube is 1.1 mm or between about 0.8 and 1.4 mm, the outer diameter is about 2.1 mm or between about 1.8 mm and 2.4 mm, the overall length of the tube 400 is about 2.2 mm or between about 1.8 and 2.6 mm, and the helical pitch is 0.44 mm or between about 0.35 and 0.55 mm.

The tympanic membrane equalization tubes disclosed herein can include features which help recover a misplaced tympanic membrane equalization tube. A misplaced tympanic membrane equalization tube located distally to the tympanic membrane can be especially difficult to remove. Such features can include tethers attached to any portion of the tympanic membrane equalization tubes. The tethers can be grasped proximally to the tympanic membrane and used to pull the misplaced tympanic membrane equalization tube out of the ear.

In general, methods for inserting pressure equalization tubes into the tympanic membrane include both simple, manual methods and more complicated, automatic systems for making an incision and placing the tube into the incision. A manual method for inserting a pressure equalization tube into a tympanic membrane includes placing a speculum into the ear canal in apposition with the tympanic membrane in order to more clearly visualize the membrane. Following visualization of the tympanic membrane, a myringotomy blade is inserted into the speculum and a small incision is created in the tympanic membrane (a myringotomy) to relieve pressure caused by the excessive buildup of fluid due to infection in the middle ear. Forceps are then used to collapse the pressure equalization tube and insert it into the incision to allow external ventilation of the middle ear for an extended period of time. Suction may be applied before or after tube insertion in order to remove the fluid in the middle ear.

Figure 14:
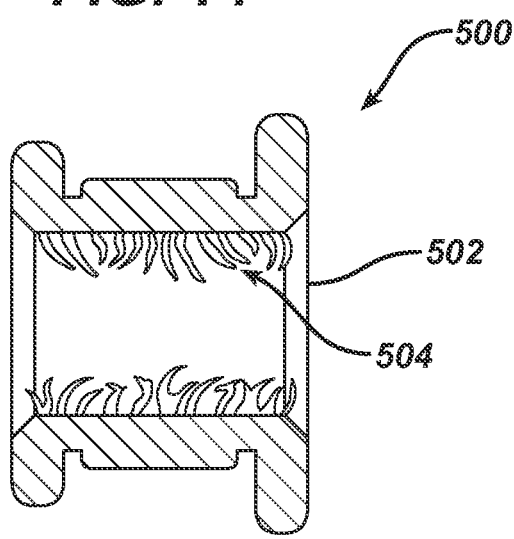
FIG. 14 is a side view of a pressure equalization tube according to still another embodiment of the invention.
Figure 15:
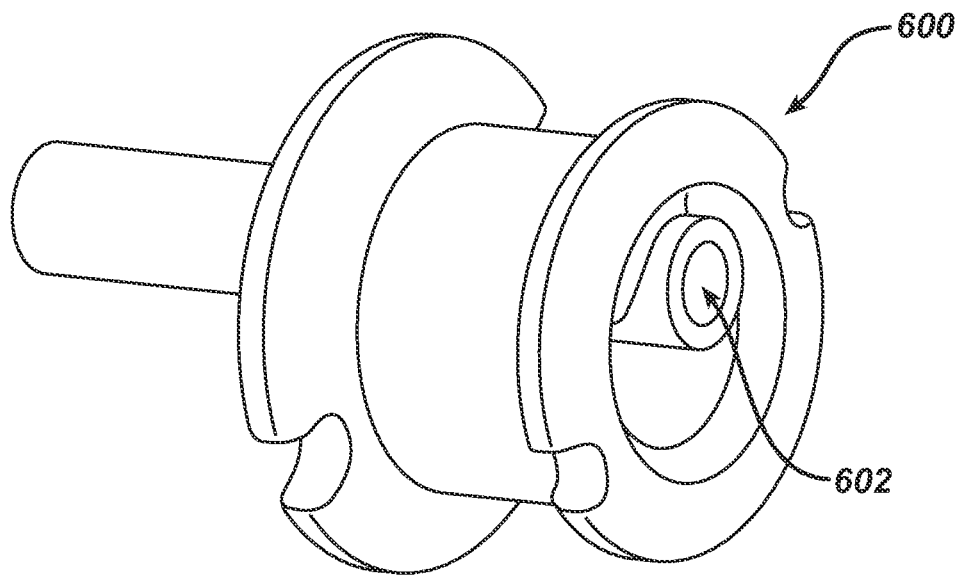
FIG. 15 is a perspective view of a pressure equalization tube according to a further embodiment of the invention.
Figure 16:
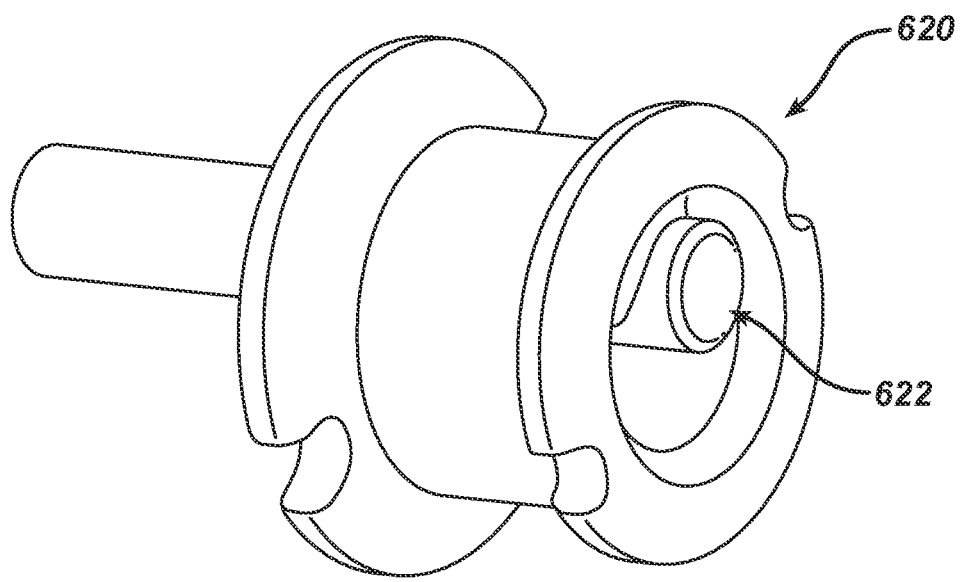
FIG. 16 is a perspective view of another pressure equalization tube embodiment according to the invention.

Rather than applying suction after tube insertion, according to the embodiments shown in FIGS. 14, 15 and 16 effusion removal systems are incorporated with the pressure equalization tube. The pressure equalization tube 500 shown in FIG. 14 has an open lumen 502 lined with artificial cilia 504 to aid the transport and expulsion of effusion from the middle ear. The artificial cilia may include microtubules and molecular motors that create waves or beating action to transport the effusion or other bodily fluids through the lumen 502 of the tube 500. Such cilia are described in detail in Sanchez, Timothy et al; Cilia-like Beating of Active Microtubule Bundles; Science 22 July 2011; Vol. 333 no. 6041 pp. 456-459, or U.S. Pat. No. 6,849,910 which describes a similar mechanism for surface fluid transport using oscillatory MEMs. Both publications are incorporated by reference herein in their entirety.

FIG. 15 shows a pressure equalization tube 600 with a vent lumen 602 and FIG. 16 shown a pressure equalization tube 620 with a wick 622 that would aid in effusion removal during deployment of the pressure equalization tubes by allowing effusion to be vented or wicked from the ear canal. Further, in the event that the physician desires to use suction to remove the effusion, an air return path is provided, breaking the effect of vacuum in a closed space.

Systems for automatically puncturing and delivering the tympanic membrane pressure equalization tubes into atympanic membrane are described in US Patent Publication No. 2011/0015645, which is incorporated herein in its entirety and in US Patent Publication No. 2009/0209972. These methods generally include grasping a housing with a dedicated handgrip, or a graspable housing. A shaft extends out of the housing to access the tympanic membrane, and the method includes loading a tympanic membrane equalization tube within the tip of the shaft resulting in a compressed tympanic membrane equalization tube. The tip of the shaft of the graspable housing is then brought into contact with the tympanic membrane. An internal spring loaded cam-based mechanism is located within the housing and coupled to a button. The method further includes triggering a mechanism which results in puncturing the tympanic membrane. Following puncturing the tympanic membrane, the method involves delivering the tympanic membrane pressure equalization tube. The tympanic membrane pressure equalization tube that has been folded or compressed within the tube and recovers its shape into its uncompressed shape when delivered into the tympanic membrane. The size and shape of the medial flange retention elements are optimal for ensuring that the tympanic membrane pressure equalization tube can be inserted through a myringotomy in a tympanic membrane. The retention elements are longitudinally aligned with the tubular body lumen and do not overlap one with the other, limiting the cylindrical profile of the tube in the compressed state, and optimizing recovery to the perpendicular alignment of the retention elements and the tubular body lumen in the uncompressed state. Further, the size and shape of the lateral flange retention elements ensure that the lateral flange is retained on the lateral side of the tympanic membrane following delivery of the pressure equalization tube into the tympanic membrane, through the myringotomy.

Figure 17:
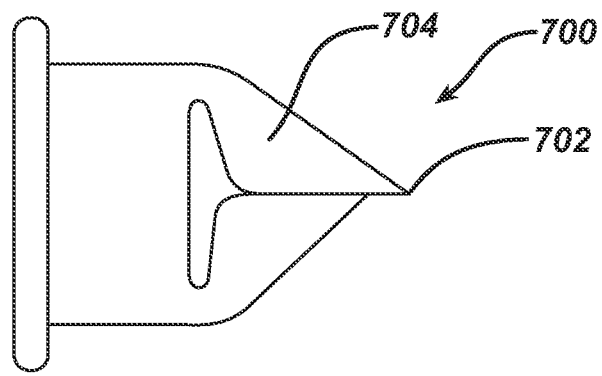
FIG. 17 is a side view of a pressure equalization tube according to another embodiment of the invention in its unexpanded state.
Figure 18:
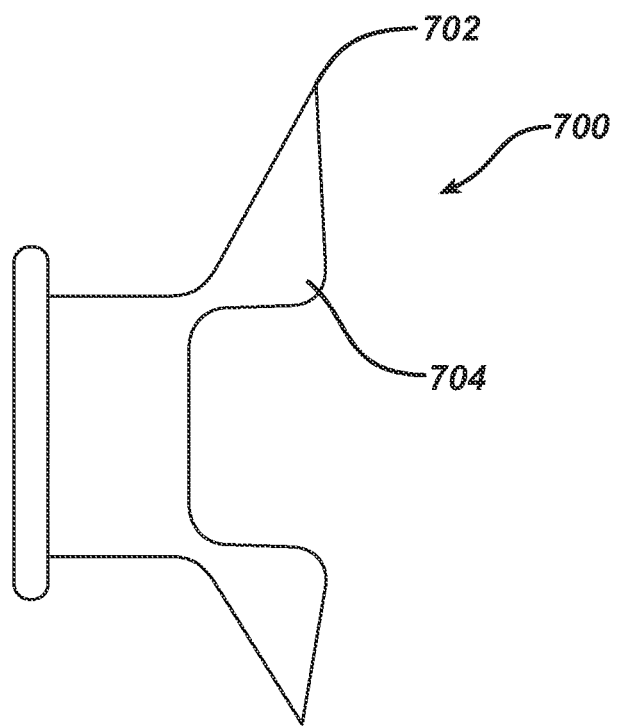
FIG. 18 is a side view of the tube of FIG. 17 in its expanded state.

Another embodiment of a pressure equalization tube 700 according to the invention includes a cutting tube with sufficient rigidity (i.e. fabricated from a shape memory material such as nitinol or PEEK shape memory polymer) to make a myringotomy when pushed into the tympanic membrane without the use of additional delivery systems. The tube is pre-shaped with conventional heat/cool methods such that it is normally closed prior to use with a sharp cutter edge 702 centered on the medial flange 704 (see FIG. 17). The medial flange, when closed is taper shaped, and will therefore self-dilate when pushed in place. After placement, the tube will be self-anchoring, that is, the medial flange 704 will expand as a result of body heat (See FIG. 18). The tube medial flange dilation can be controlled with a cold mandrel inserted into the tube to keep the tube in a closed shape for safe insertion, and then allow for self-anchoring when the mandrel is removed. For extraction of the tube, the cold mandrel can be re-inserted into the tube so that it will return to its closed shape (as shown in FIG. 17), thereby minimizing the risk of damaging the tympanic membrane from the expanded anchoring flange.

While preferred embodiments of the present invention have been shown and described herein, it will be obvious to those skilled in the art that such embodiments are provided by way of example only. Numerous variations, changes and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. An apparatus, comprising:
   a tubular body defining a proximal end, a distal end, an interior wall, and an exterior surface, the tubular body configured to be deployed in a tympanic membrane;
   a first flange disposed at the distal end of the tubular body;
   a fluid transport element coupled to the interior wall and extending at least a length of the tubular body; and
   a lumen through the tubular body, the lumen distinct from the fluid transport element, and the lumen shares a common wall with the fluid transport element;
   the first flange configured to transition from a first state in which the first flange abuts the exterior surface of the tubular body and a second state in which the first flange retains the tubular body in an incision formed the tympanic membrane after deployment;
   the fluid transport element configured to enable transport of a fluid across the tympanic membrane.

2. The apparatus of claim 1, wherein the fluid transport element includes a wick.

3. The apparatus of claim 1, wherein the fluid transport element defines a vent.

4. The apparatus of claim 1, wherein the fluid transport element extends beyond at least one of the proximal end or the distal end of the tubular body.

5. The apparatus of claim 1, wherein a longitudinal axis of the fluid transport element is radially offset from a longitudinal axis of the tubular body.

6. The apparatus of claim 1, wherein the fluid transport element is configured to remove a liquid from the ear canal when the tubular body is deployed in the tympanic membrane.

7. The apparatus of claim 1, wherein the tubular body includes:
   a second flange disposed at the proximal end of the tubular body,
   the first flange and the second flange collectively configured to retain the tubular body in the incision formed in the tympanic membrane.

8. The apparatus of claim 7, wherein at least one of the first flange or the second flange has an outer diameter greater than an outer diameter of the other of the first flange or the second flange.

9. The apparatus of claim 7, wherein at least one of the first flange or the second flange includes at least one notch configured to allow the at least one of the first flange or the second flange to be folded down and disposed within the introducer.

10. The apparatus of claim 9, wherein the first flange has a first notch and the second flange has a second notch, the first notch aligned with the second notch.

11. The apparatus of claim 7, wherein the first flange and the second flange are each deformable such that the tubular body can be disposed within the introducer.

12. The apparatus of claim 7, wherein the first flange and the second flange are aligned along a longitudinal length of the tubular body in the first state and aligned perpendicular to the longitudinal length of the tubular body in the second state.

13. The apparatus of claim 1, wherein the tubular body is formed of a shape memory material and can be compressed from the second state into the first state and disposed within the introducer and can revert back to the second state when the tubular body is deployed in the tympanic membrane.

14. The apparatus of claim 1, further comprising a suction device configured to apply a suction to remove a liquid in a middle ear disposed adjacent to the tympanic membrane.

15. The apparatus of claim 14, wherein the fluid is air, the fluid transport element configured to prevent a vacuum from forming within the middle ear.

16. A method, comprising:
    compressing a tubular body into a first state such that the tubular body can be disposed within an introducer, the tubular body including a fluid transport element through the tubular body and a lumen through the tubular body, and the lumen shares a wall with the fluid transport element;
    advancing the introducer and the tubular body in the first state into an ear canal;
    forming an incision in a tympanic membrane disposed adjacent to the ear canal;
    placing the tubular body in the incision such that a distal end of the tubular body is disposed distal to the tympanic membrane in a middle ear and a proximal end of the tubular body is disposed proximal to the tympanic membrane in the ear canal; and
    transporting a fluid from the ear canal into the middle ear via the fluid transport element.

17. The method of claim 16, further comprising:
    applying a suction to remove a liquid in the middle ear, the transporting including providing an air transport path into the middle ear.

18. The method of claim 16, wherein the fluid transport element includes a wick.

19. The method of claim 16, wherein the fluid transport element defines a vent.

* * * * *